United States Patent [19]
Bailly et al.

[11] Patent Number: 6,030,953
[45] Date of Patent: Feb. 29, 2000

[54] PHARMACEUTICAL COMPOSITION CONTAINING CHITOSAN

[75] Inventors: Jacques Bailly, Rixheim, France; André Fleury, Gempen, Switzerland; Paul Hadvary, Biel-Benken, Switzerland; Hans Lengsfeld, Basel, Switzerland; Hans Steffen, Liestal, Switzerland

[73] Assignee: Hoffmann-La Roche Inc., Nutley, N.J.

[21] Appl. No.: 09/370,845

[22] Filed: Aug. 10, 1999

[30] Foreign Application Priority Data

Aug. 14, 1998 [EP] European Pat. Off. ............... 98115310
May 11, 1999 [EP] European Pat. Off. ............... 99109430

[51] Int. Cl.$^7$ .......................... A61K 31/70; A61K 31/73; A61K 31/335
[52] U.S. Cl. .............................. 514/25; 514/55; 514/449; 514/922
[58] Field of Search ............................... 514/25, 55, 449, 514/922

[56] References Cited

U.S. PATENT DOCUMENTS 4,598,089 7/1986 Hadvary et al. ........................ 514/449
5,447,953 9/1995 Isler et al. ............................. 514/449

OTHER PUBLICATIONS

CA 116:120739, Hauptman et al., 1992.
CA106:155279, Hager et al., 1986
CA 125:184841, Melia et al., 1996.
CA 129:90278, Van Gaal, et al., 1998.

*Primary Examiner*—Kimberly Jordan
*Attorney, Agent, or Firm*—George W. Johnson; William H. Epstein; Briana C. Buchholz

[57] ABSTRACT

The present invention provides orally administrable pharmaceutical compositions containing an inhibitor of gastrointestinal lipase, and at least one compound selected from the group consisting of chitosan, its derivatives and salts thereof. Methods are provided for preventing and treating anal leakage of oil in a patient to whom a composition containing an inhibitor of gastrointestinal lipase is orally administered.

23 Claims, No Drawings

PHARMACEUTICAL COMPOSITION CONTAINING CHITOSAN

BACKGROUND OF THE INVENTION

The present invention relates to pharmaceutical compositions containing an inhibitor of gastrointestinal lipase, and at least one compound selected from the group consisting of chitosan, its derivatives and salts thereof.

An example of an inhibitor of gastrointestinal lipase is orlistat, previously known as tetrahydrolipstatin or THL. It reduces the absorption of dietary fat. Its use for the control or prevention of obesity and hyperlipaemia, is described in U.S. Pat. No. 4,598,089. Orlistat is the N-formyl-L-leucine ester with (3S,4S)-3-hexyl-4-[(2S)-2-hydroxytridecyl]-2-oxetanone.

Anal leakage of oil (oily spotting) is an adverse effect which is occasionally observed in patients treated with lipase inhibitors. It results from physical separation of some liquid unabsorbed dietary fat from the bulk of the fecal mass in the lower large intestine. This effect can be prevented with the pharmaceutical compositions of the present invention.

In U.S. Pat. No. 5,447,953 it has been demonstrated that by combining a lipase inhibitor with substantial amounts of water insoluble crude fibers, the inhibiting effect on fat absorption can be increased.

SUMMARY OF THE INVENTION

Surprisingly, it has now been found that by combining a lipase inhibitor with low amounts of chitosan or a derivative or a salt thereof, the phenomenon of anal leakage of oil can be strongly reduced. The present invention is directed to pharmaceutical compositions containing an inhibitor of gastrointestinal lipase, and at least one compound selected from the group consisting of chitosan, its derivatives and salts thereof. The compositions of the present invention also optionally include auxiliary excipients.

The present invention is also concerned with the use of chitosan or a derivative or a salt thereof for the combined simultaneous, separate or chronologically spaced use with an inhibitor of gastrointestinal lipase, such as orlistat, in the treatment of obesity and hyperlipaemia and their comorbidities, such as type II diabetes mellitus.

Artificial non-absorbed fats, mostly sucrose polyester, are used in the food industry for the production of low fat foods, such as low fat potato potato chips, low fat cookies, low fat salad dressings and low fat ice cream. The ingestion of higher amounts of such foodstuffs containing non-absorbable fats can induce oily leakage.

The pharmaceutical compositions of the present invention reduce fat absorption through inhibition of gastrointestinal lipase. The invention is further concerned with the use of chitosan or a derivative or a salt thereof for treating or preventing the syndrome of anal leakage of oil occurring after the administration of an inhibitor of gastrointestinal lipase, such as orlistat, or after ingestion of food containing poorly absorbable or non-absorbable fats or oils or of undigestible oily fat substitutes.

Methods are provided for treating or preventing the syndrome of anal leakage of oil in a patient to whom a composition containing an inhibitor of gastrointestinal lipase is orally administered in unit dosage form.

DETAILED DESCRIPTION OF THE INVENTION

Chitosan is derived from chitin, a polysaccharide composed of (1→4)-linked 2-acetamido-2-deoxy-β-D-glucopyranosyl residues isolated from natural sources, by complete or partial deacetylation and partial depolymerization. Chitosan has a molecular weight of the order of $10^4$ to $10^5$. Chitosan is soluble at gastric pH and insoluble or gel-like at intestinal pH. Examples of chitosan derivatives are medium or long chain N-alkyl- or N-alkanoyl-chitosan. The term "medium chain N-alkyl- or N-alkanolyl" refers to $C_{8-13}$-N-alkyl- or -N-alkanolyl chains, the term "long chain N-alkyl- or N-alkanoyl" refers to $C_{14-18}$-N-alkyl- or -N-alkanolyl chains. Any conventional salts of chitosan can be utilized in accordance with this invention. Examples of salts of chitosan are those with organic acids such as lower alkanoic acids, as well as mineral acids such as HCl and $H_2SO_4$. Any conventional pharmaceutically acceptable acid of chitosan can be utilized such as acetic, citric, formic and tartaric acid.

Synonyms of chitosan (the Merck Index, 11th ed., #2052, 1989) are poly-D-glucosamine; poly-[1→4]-β-D-glucosamine and deacetylated chitin. The deacetylation of chitin which has the formula

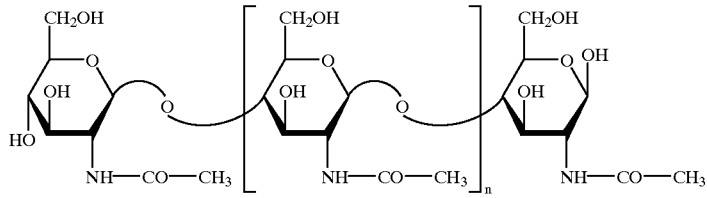

to chitosan of the formula

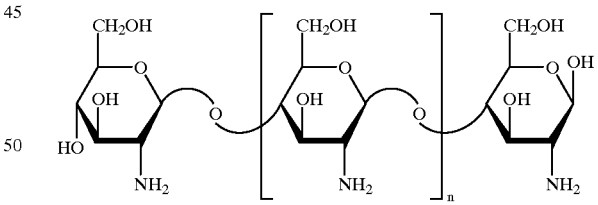

can be performed in hot concentrated NaOH solution (40–50%). Chitosan is commercially available from Pronova Biopolymer, Inc., 135 Commerce Way, Suite 201, Portsmouth, NH03801, e.g. as SEACURE 142, 242 or 342 with a viscosity interior to 20 cps, from 20 to 200 cps and from 200 to 800 cps, respectively.

Examples of lipase inhibitors which can be used in the compositions of the present invention are orlistat, lipstatin, panclicins, hesperidin, ebelactones, esterastin and their derivatives, and valilactone. The most preferred lipase inhibitor is orlistat.

Any conventional auxiliary excipients can be used in formulating the dosage forms of the present invention. Examples of auxiliary excipients which can be used in the pharmaceutical compositions of the invention are binders, diluents and lubricants, such as AVICEL, polyvinyl pyrrolidone (povidone), talc and sodium stearyl fumarate; sweeteners, such as sorbitol, glucose, saccharose, saccharine-sodium salt and sodium cyclamate; flavour agents, such as passion fruit, citron and limette; flavour enhancers, such as citric acid, monosodium citrate, sodium chloride and chinine sulfate; effervescing agents, such as sodium bicarbonate and tartaric acid, disintegrants, antimicrobial agents, such as p-hydroxybenzoic acid methyl or propyl ester; detergents and colouring agents, such as β-carotene.

AVICEL essentially comprises microcrystalline cellulose. It is available from FMC Corporation, Pharmaceutical Division, 1735 Market Street, Philadelphia, Pa. 19103, e.g. as AVICEL RC-591 or CL-611, which are mixtures of microcrystalline cellulose (about 92%) and carboxymethyl-cellulose sodium (about 8%), AVICEL PH 101 or PH 105, which is microcrystalline cellulose with an average particle size of 50 or 20µ, respectively; AVICEL CE-15 a mixture of microcrystalline cellulose and guar gum.

The superiority of chitosan over microcrystalline cellulose, e.g. AVICEL, in reducing anal leakage of oil is shown in the following experiment:

The experiment for loss of free fecal oil is based on the observation that mice, due to steadily grooming their furs, distribute any excreted free fecal oil all over their bodies. This results in an easily visible brownish coloring of the fur (oily fur greasing). In mice weighing 20–25 g, excretion of free oil was provoked by administering an excessive dose of orlistat (300 µmol/kg/day) together with a diet containing 7% fat, resulting in a daily fat intake of 1 g/day. The diet consisted of mashed Hamburger, butter, French fries and string beans.

The following time schedule of treatment was followed:
days 1–5: feeding groups of 3 mice on the above diet and food additives (increasing doses of chitosan or AVICEL), and a control group without food additives
days 3–4: adding orlistat (300 µmol/kg/day)
day 5: registration by photography of oily fur greasing Oily fur greasing was evaluated by daily scoring units 1 to 4:
1 representing 0–25% skin involvement, 2: 26–50% skin involvement, 3: 50–75% and 4: 75–100% skin involvement.

The skin involvement of the individual mice was added up for days 3–5. (At e.g. 100% skin involvement for days 3–5 the scoring would be maximal, i.e. 4+4+4=12 units). The oily fur greasing score in the controls was 6.3±1.6 units (mean±SE).
In 7 groups of mice receiving chitosan or AVICEL against oily fur greasing, its extent was first evaluated according to the scoring above, then expressed in % of the control groups and finally averaged within the animals of each group. The results are given in the table below: Oily fur greasing (% of controls) in mice ingesting orlistat (300 µmol/kg/day)

| food additive (g/100 g feed) | chitosan | AVICEL |
|---|---|---|
| 15 | n.d. | 17 ± 4 |
| 10 | n.d. | 29 ± 7 |
| 5 | n.d. | 53 ± 24 |
| 3 | 6 ± 3 | n.d. |
| 1 | 37 ± 16 | n.d. |
| 0.3 | 53 ± 5 | n.d. |
| 0.1 | 63 ± 9 | n.d. | n.d. = not determined

When the diet contained chitosan, the extent of oily fur greasing was reduced. For instance, as compared to controls, the same 53% inhibition of oily fur greasing is obtained with a feed containing as much as 5 weight % of AVICEL and only 0.3 weight % of chitosan.

The compositions of the present invention reduce fat absorption in a patient through the use of a gastrointestinal lipase inhibitor to inhibit gastrointestinal lipase. The compositions also treat and prevent the syndrome of anal leakage of oil that can occur in a patient upon administration of the gastrointestinal lipase inhibitor. The compositions of the invention conveniently contain from 10 to 50, preferably from 20 to 40, parts by weight of chitosan or a derivative or a salt thereof and from 10 to 200, preferably from 20 to 80, parts by weight of auxiliary excipients for 1 part by weight of an inhibitor of gastrointestinal lipase, such as orlistat. The inhibitor of gastrointestinal lipase in the compositions of the invention is present in an amount at least sufficient to reduce the absorption of fat in the meal consumed by a patient.

The composition of the invention can also be in form of a commercial pack containing an inhibitor of gastrointestinal lipase and chitosan or a derivative or a salt thereof, with instructions for its use for the simultaneous, separate or chronologically spaced use in the treatment of obesity or hyperlipaemia.

For the treatment or prevention of obesity or hyperlipaemia, a composition of the invention containing from 10 mg to 500 mg of an inhibitor of gastrointestinal lipase, such as orlistat, and from 500 mg to 20 g, preferably from 2 g to 10 g, of chitosan or a derivative or a salt thereof, can be administered orally once, twice or three times per day.

The compositions of the invention can be administered to patients in oral dosage forms. For example, the compositions can be administered as drinkable formulations, such as solutions or suspensions prepared from powder, granules, pellets, tablets to be reconstituted or effervescent tablets; or in form of chewable formulations, such as tablets, capsules or lozenges. They can also be incorporated into food preparations, such as wafers, crackers or bread, or can be in form of swallowable formulations, such as tablets or capsules.

A preferred composition of the invention is a tablet for the treatment of obesity, consisting essentially of orlistat as the active ingredient and chitosan, wherein the dosage is from 10 to 120 mg of orlistat and from 0.5 to 5 g of chitosan. Most preferably, the tablet consists essentially of about 60 mg of orlistat and about 2.5 g of chitosan. Preferably, the tablet is chewable.

A further preferred composition of the invention is a wafer for the treatment of obesity, consisting essentially of orlistat as the active ingredient and chitosan, wherein the dosage is from 10 to 200 mg of orlistat and from 1 to 10 g of chitosan. Most preferably, the wafer consists essentially of about 120 mg of orlistat and about 5 g of chitosan.

In accordance with the present invention, methods are provided for treating or preventing the syndrome of anal leakage of oil in a patient to whom a composition containing an inhibitor of gastrointestinal lipase is being orally administered in unit dosage form. Treating or preventing the syndrome of anal leakage of oil in a patient is accomplished by orally administering to a patient per meal consumed by the patient a composition in unit dosage form containing an inhibitor of gastrointestinal lipase, and at least one compound selected from the group consisting of chitosan, its derivatives and salts thereof The gastrointestinal lipase inhibitor is present in this composition in an amount at least sufficient to reduce the absorption of fat in the meal consumed by a patient. In general, this amount is preferably, from about 10 mg to about 500 mg. The chitosan compound is preferably present in the unit dosage form in an amount of from about 500 mg to about 20 g.

A preferred method of treating or preventing the syndrome of anal leakage of oil occasionally occurring after the oral administration of a lipase inhibitor, comprises orally administering a lipase inhibitor, preferably orlistat, and chitosan in a dosage amount from 10 to 200 mg of lipase inhibitor and from 0.5 to 10 g of chitosan per fat containing meal. Most conveniently, this method comprises orally administering to a patient a composition in unit dosage form containing orlistat and chitosan, the dosage amount is from 10 to 120 mg of orlistat and from 2 to 6 g of chitosan, particularly about 60 mg of orlistat and about 2.5 g of chitosan per fat containing meal consumed by the patient. Preferably, the composition is orally administered to the patient at breakfast, lunch and dinner.

The following non-limiting examples illustrate pharmaceutical preparations that can be produced by conventional procedures:

EXAMPLE 1

Chitosan granules or pellets for the simultaneous, separate or chronologically spaced administration of orlistat are prepared as follows:

50 g of chitosan (SEACURE 342) and 50 g of AVICEL RC-591 are mixed and kneaded with demineralized water to a suitable consistency. The wet mass is sieved and then dried in a fluidized bed to give granules. Alternatively the wet mass is extruded and spheronized and then dried in a fluidized bed to give pellets. A quantity of 5 g or 1 0 g of granules or pellets is filled into sachets as unit dose. Alternatively, this material is filled into appropriate containers. The dosing may be performed with appropriate spoons.

EXAMPLE 2

| Powder for reconstitution: | |
| --- | --- |
| Orlistat | 0.12 g |
| Low viscosity chitosan (SEACURE 142) | 5 g |
| Sorbitol | 7.11 g |
| AVICEL CL 611 | 1.20 g |
| β-carotene | 0.06 g |
| Citric acid | 0.10 g |
| p-Hydroxybenzoic acid methyl ester | 0.15 g |
| p-Hydroxybenzoic acid propyl ester | 0.03 g |
| Flavouring agent (passion fruit) | 0.13 g |
| AVICEL PH 105 | 8.00 g |
| Monosodium citrate | 1.00 g |
| Saccharine-sodium salt | 0.10 g |
| Total | 23 g |

An oral suspension is obtained by adding tap-water to the above powder to a volume of about 100 ml.

EXAMPLE 3

| Granulates or pellets: | |
| --- | --- |
| Orlistat | 0.120 g |
| Chitosan (SEACURE 242) | 5.0 g |
| AVICEL PH 101 | 4.88 g |

The above ingredients are mixed and kneaded with demineralized water to obtain a suitable consistency. The wet mass is sieved and dried in a fluidized bed at a temperature below 35° C. to give granules. Alternatively, the wet mass is extruded and spheronized and then dried in a fluidized bed to give pellets. A quantity of 10 g the granules or pellets is filled into sachets as unit dose. Alternatively, the material is filled into appropriate containers. The dosing can be performed with appropriate spoons.

EXAMPLE 4

| Effervescent tablets: | |
| --- | --- |
| Orlistat | 0.120 g |
| Saccharose powder | 1.669 g |
| Low viscosity chitosan (SEACURE 142) | 2.5 g |
| Sodium cyclamate | 0.115 g |
| Saccharine sodium salt | 0.004 g |
| Sodium bicarbonate | 0.7 g |
| Tartaric acid (crystallized) | 1.12 g |
| Sodium chloride (milled) | 0.04 g |
| Chinine sulfate | 0.007 g |
| Flavoring agent | 0.025 g |
| Total | 6.3 g |

Orlistat, saccharose, chitosan, sodium cyclamate and saccharin sodium are mixed and sieved. The mixture is kneaded with a mixture of ethanol and demineralized water, granulated and dried at a temperature below 35° C. in a fluidized bed to give a mixture A. Sodium bicarbonate, tartaric acid, sodium chloride, chinine sulfate and the flavoring agent are mixed and sieved to give a mixture B. A and B are mixed and compressed to effervescent tablets of 6.3 g and a diameter of 30 mm.

EXAMPLE 5

| Chewable tablets: | |
| --- | --- |
| Orlistat | 0.060 g |
| Chitosan (SEACURE 242) | 2.5 g |
| Sorbitol | 1.84 g |
| AVICEL CE-15 | 1.0 g |
| Talc | 0.480 g |
| Sodium stearyl fumarate | 0.120 g |
| Total | 6.0 g |

Orlistat, chitosan, sorbitol and AVICEL CE-1 5 are mixed and sieved. Talc and sodium stearyl fumarate are sieved and mixed with the first obtained mixture and then compressed to chewable tablets of 6.0 g and a diameter of 2 cm.

EXAMPLE 6

Chitosan wafers for the simultaneous, separate or chronologically spaced administration of orlistat are prepared as follows:

Corn flour (5 g) and 5 g of chitosan are mixed. Soybean oil (2 g) is added and the mixture is mixed for 15 minutes. Water is added to form a wet mass which is then extruded. The wet wafers are dried in an oven at 35° C. and then packaged.

EXAMPLE 7

| Wafers: | |
| --- | --- |
| Chitosan | 5 g |
| Soybean oil | 2 g |
| Corn flour | 5 g |
| Orlistat | 120 mg |

The process is the same as in Example 6 but orlistat is first dissolved in soybean oil and added to the blend. After the wet massing with water and extrusion, the wafers are dried at 35° C.

EXAMPLE 8

Wafers: the proportions of the ingredients and the procedure are the same as in Example 7, but molten tripalmitin is substituted for soybean oil.

EXAMPLE 9

Chitosan wafers for the simultaneous, separate or chronologically spaced administration of orlistat are prepared as follows:

Chitosan (5 g) and 5 g of maltodextrin are mixed. Molten tripalmitin (2 g) is added to the mixture. The mass is then wetted with water and the wet mass is extruded. The wafers are dried at 35° C.

EXAMPLE 10

| Wafers: | |
| --- | --- |
| Chitosan | 5 g |
| Maltodextrin | 5 g |
| Triplamitin | 2 g |
| Orlistat | 120 mg |

The process is the same as in Example 9 but orlistat is dissolved in molten tripalmitin and then added to the blend. The wafers are dried at 35° C.

We claim:

1. A pharmaceutical composition in unit dosage form, said composition comprising an inhibitor of gastrointestinal lipase, and at least one compound selected from the group consisting of chitosan, its derivatives and salts thereof, wherein said composition contains 10 to 50 parts by weight of the compound per 1 part by weight of the inhibitor of gastrointestinal lipase.

2. The composition according to claim 1, wherein the compound is present in an amount of from about 500 mg to about 20 g and the inhibitor of the gastrointestinal lipase is present in an amount of from about 10 mg to about 500 mg.

3. The composition according to claim 2, wherein the compound is present in an amount of from about 2 g to about 10 g and the inhibitor of gastrointestinal lipase is present in an amount of from about 10 mg to about 500 mg.

4. The composition according to claim 1, wherein the inhibitor of gastrointestinal lipase is orlistat.

5. The composition according to claim 1, wherein the compound is chitosan.

6. The composition according to claim 1, wherein the unit dosage form is an oral dosage form.

7. The composition according to claim 6, wherein the oral dosage form is selected from the group consisting of tablets, capsules, lozenges, liquid formulations, wafers and crackers.

8. The composition according to claim 2, wherein the compound is chitosan and the inhibitor of gastrointestinal lipase is orlistat, said chitosan being present in the composition in an amount of from about 0.5 g to about 5 g and said orlistat being present in the composition in an amount of from about 10 mg to about 120 mg.

9. The composition according to claim 8, wherein said unit dosage form is a tablet.

10. The composition according to claim 9, wherein the tablet contains about 2.5 g of chitosan and about 60 mg of orlistat.

11. The composition according to claim 3, wherein the unit dosage form is a wafer containing from about 1 g to about 10 g of chitosan and from about 10 mg to about 200 mg of orlistat.

12. The composition according to claim 11, wherein the wafer contains about 5 g of chitosan about 120 mg of orlistat.

13. The composition according to claim 1, wherein the composition contains at least one auxiliary excipient.

14. A pharmaceutical composition in unit dosage form for reducing fat absorption through inhibition of gastrointestinal lipase, said composition comprising an inhibitor of gastrointestinal lipase, said inhibitor of gastrointestinal lipase being present in the composition in an amount at least sufficient to reduce absorption of fat in a meal consumed by the patient; and at least one compound selected from the group consisting of chitosan, its derivatives and salts thereof, wherein said composition contains 10 to 50 parts by weight of the compound per 1 part by weight of the inhibitor of gastrointestinal lipase.

15. The composition according to claim 14, wherein the compound is present in an amount of from about 500 mg to about 20 g and the inhibitor of the gastrointestinal lipase is present in an amount of from about 10 mg to about 500 mg.

16. The composition according to claim 15, wherein the compound is present in an amount of from about 2 g to about 10 g and the inhibitor of gastrointestinal lipase is present in an amount of from about 10 mg to about 500 mg.

17. The composition according to claim 16, wherein the inhibitor of gastrointestinal lipase is orlistat.

18. The composition according to claim 14, wherein the compound is chitosan.

19. The composition according to claim 14, wherein the unit dosage form is an oral dosage form.

20. A method of treating or preventing the syndrome of anal leakage of oil in a patient to whom a composition containing an inhibitor of gastrointestinal lipase is being orally administered in unit dosage form, comprising orally administering to a patient per meal consumed by the patient a composition in unit dosage form containing an inhibitor of gastrointestinal lipase present in an amount at least sufficient to reduce absorption of fat in a meal consumed by the patient, said inhibitor of gastrointestinal lipase being present in an amount of from about 10 mg to about 500 mg, and at least one compound selected from the group consisting of chitosan, its derivatives and salts thereof, said compound being present in the unit dosage form in an amount of from about 500 mg to about 20 g.

21. The method according to claim 20 wherein said composition in unit dosage form contains from about 0.5 g to about 10 g of chitosan and from about 10 mg to about 200 mg of orlistat.

22. The method of claim 21, wherein said composition in unit dosage form contains from about 2 g to about 6 g of chitosan and from about 10 mg to about 120 mg of orlistat.

23. The method of claim 22, wherein said composition in unit dosage form contains about 2.5 g of chitosan and about 60 mg of orlistat.

* * * * *